(12) United States Patent
Leyva et al.

(10) Patent No.: US 11,819,585 B2
(45) Date of Patent: Nov. 21, 2023

(54) TECHNOLOGIES FOR SANITIZING MIST HUMIDIFIERS

(71) Applicant: SoClean, Inc., Peterborough, NH (US)

(72) Inventors: Timothy Leyva, Bellingham, MA (US); William E. Olszta, Webster, MA (US); Tahira Jayasuriya, Peterborough, NH (US)

(73) Assignee: SOCLEAN, INC., Peterborough, NH (US)

( * ) Notice: Subject to any disclaimer, the term of this patent is extended or adjusted under 35 U.S.C. 154(b) by 684 days.

(21) Appl. No.: 16/553,773

(22) Filed: Aug. 28, 2019

(65) Prior Publication Data

US 2019/0388575 A1 Dec. 26, 2019

Related U.S. Application Data

(63) Continuation of application No. 15/499,378, filed on Apr. 27, 2017, now Pat. No. 10,434,204, which is a
(Continued)

(51) Int. Cl.
*A61L 2/20* (2006.01)
*F24F 6/12* (2006.01)
(Continued)

(52) U.S. Cl.
CPC ............ *A61L 2/202* (2013.01); *A61L 2/183* (2013.01); *A61L 2/24* (2013.01); *F24F 6/12* (2013.01);
(Continued)

(58) Field of Classification Search
CPC ..................................................... A61L 2/202
See application file for complete search history.

(56) References Cited

U.S. PATENT DOCUMENTS 4,019,986 A * 4/1977 Burris ...................... C02F 1/78
210/220
4,035,657 A 7/1977 Carlson
(Continued)

FOREIGN PATENT DOCUMENTS

CN 1377708 11/2002
CN 2710637 7/2005
(Continued)

OTHER PUBLICATIONS

Ozone MSDS (Material Safety Data Sheets), Ozone Solutions, Jun. 1, 2000, http://www.ozoneapplications.com/info/ozone_msds.htm, 5 pages.
(Continued)

*Primary Examiner* — Donald R Spamer
(74) *Attorney, Agent, or Firm* — Grossman, Tucker, Perreault & Pfleger, PLLC

(57) ABSTRACT

Technologies (e.g., devices, systems and methods) for sanitizing mist humidifiers are described. In some embodiments, the technologies include a sanitization gas system and a connector unit. The connector unit is configured to install into an opening in the mist humidifier that is used in operation to release mist for humidification purposes. The connector unit includes an inlet passageway for supplying sanitizing gas (e.g., ozone) into the humidifier, and an exhaust system for removing sanitizing gas from the reservoir.

9 Claims, 5 Drawing Sheets

Related U.S. Application Data continuation-in-part of application No. 15/441,929, filed on Feb. 24, 2017, now Pat. No. 10,398,797, which is a continuation of application No. 15/142,111, filed on Apr. 29, 2016, now Pat. No. 9,610,373, said application No. 15/499,378 is a continuation of application No. 15/141,152, filed on Apr. 28, 2016, now Pat. No. 10,485,888, which is a continuation-in-part of application No. PCT/US2015/029418, filed on May 6, 2015, and a continuation-in-part of application No. 14/232,773, filed as application No. PCT/US2012/046593 on Jul. 13, 2012, now Pat. No. 9,358,316, said application No. 15/142,111 is a continuation of application No. 14/232,773, filed as application No. PCT/US2012/046593 on Jul. 13, 2012, now Pat. No. 9,358,316.

(60) Provisional application No. 61/508,341, filed on Jul. 15, 2011.

(51) Int. Cl.
   *A61L 2/18* (2006.01)
   *A61L 2/24* (2006.01)

(52) U.S. Cl.
   CPC ..... *A61L 2202/121* (2013.01); *A61L 2202/14* (2013.01); *A61L 2202/24* (2013.01); *A61M 2202/0216* (2013.01); *A61M 2209/10* (2013.01)

(56) References Cited

U.S. PATENT DOCUMENTS

| | | |
|---|---|---|
| 4,110,419 A | 8/1978 | Miller |
| 4,207,291 A | 6/1980 | Byrd |
| 4,465,522 A | 8/1984 | Taldo |
| 4,517,159 A | 5/1985 | Karlson |
| D295,074 S | 4/1988 | Jerge |
| 4,743,275 A | 5/1988 | Flanagan |
| 4,787,980 A | 11/1988 | Ackermann |
| 5,029,879 A | 7/1991 | Strang |
| 5,120,512 A | 6/1992 | Masuda |
| 5,207,237 A | 5/1993 | Langford |
| 5,344,622 A | 9/1994 | Faddis |
| 5,508,006 A | 4/1996 | Gabele |
| 5,520,893 A | 5/1996 | Kasting |
| D371,203 S | 6/1996 | Deeds |
| D390,645 S | 2/1998 | Hanrahan |
| 5,761,069 A | 6/1998 | Webber |
| 5,920,075 A | 7/1999 | Whitehead |
| 6,024,066 A | 2/2000 | Nakayama |
| 6,134,806 A | 10/2000 | Dhaemers |
| 6,158,784 A | 12/2000 | Lavender |
| 6,276,304 B1 | 8/2001 | Tai |
| 6,280,633 B1 | 8/2001 | Conrad |
| 6,365,601 B1 | 4/2002 | Fournier |
| 6,379,617 B1 | 4/2002 | Spickermann |
| 6,379,632 B1 | 4/2002 | Kinoshita |
| D476,423 S | 6/2003 | Picot |
| 6,576,190 B1 | 6/2003 | Park |
| 6,605,260 B1 | 8/2003 | Busted |
| D487,315 S | 3/2004 | Picot |
| 6,752,151 B2 | 6/2004 | Hill |
| 7,022,225 B1 | 4/2006 | Clawson |
| 7,491,321 B1 | 2/2009 | Maas et al. |
| 7,520,910 B2 | 4/2009 | Tilley |
| 7,527,603 B2 | 5/2009 | An |
| 7,676,276 B2 | 3/2010 | Karell |
| 7,767,168 B2 | 8/2010 | Namespetra |
| 7,794,522 B2 | 9/2010 | Bliss |
| 7,845,350 B1 | 12/2010 | Kayyali |
| 8,051,853 B2 | 11/2011 | Berthon-Jones |
| 8,146,946 B1 | 4/2012 | Emond |
| 8,176,771 B2 | 5/2012 | Onishi |
| 8,215,465 B2 | 7/2012 | Iceberg |
| 8,431,075 B2 | 4/2013 | Fraundorfer |
| 8,431,076 B2 | 4/2013 | Fraundorfer |
| D692,155 S | 10/2013 | Matoba |
| 8,770,198 B2 | 7/2014 | Yee |
| 8,815,164 B1 | 8/2014 | Al Azemi |
| D719,673 S | 12/2014 | Leyva |
| D719,674 S | 12/2014 | Leyva |
| 8,915,380 B2 | 12/2014 | Sowerby |
| 9,022,247 B2 | 5/2015 | Enigmann |
| D733,315 S | 6/2015 | Lui |
| D733,316 S | 6/2015 | Lui |
| D748,280 S | 1/2016 | Lui |
| 9,358,311 B2 | 6/2016 | Leyva |
| 9,358,316 B2 | 6/2016 | Leyva |
| D761,142 S | 7/2016 | Golta |
| 9,402,928 B2 | 8/2016 | Tremblay |
| D776,290 S | 1/2017 | Wan |
| 9,610,373 B2 | 4/2017 | Leyva |
| 9,616,147 B2 | 4/2017 | Leyva |
| 9,669,124 B2 | 6/2017 | Leyva |
| D802,788 S | 11/2017 | Cormier |
| 9,895,461 B2 | 2/2018 | Leyva |
| 9,907,872 B2 | 3/2018 | Schmidt |
| D819,190 S | 5/2018 | Cormier |
| 10,052,397 B2 | 8/2018 | Leyva |
| 10,232,072 B2 | 3/2019 | Leyva |
| 10,264,913 B2 | 4/2019 | Leyva |
| 10,398,797 B2 | 9/2019 | Leyva |
| 10,427,961 B2 | 10/2019 | Leyva |
| 10,434,204 B2 | 10/2019 | Leyva |
| 10,434,205 B2 | 10/2019 | Leyva |
| 10,456,492 B2 | 10/2019 | Leyva |
| 10,485,888 B2 | 11/2019 | Schmidt |
| 10,842,897 B2 | 11/2020 | Schwartz |
| 10,980,905 B2 | 4/2021 | Bohman |
| 11,000,611 B1 | 5/2021 | He |
| 2002/0139124 A1 | 10/2002 | Palermo |
| 2003/0000966 A1 | 1/2003 | Shelton |
| 2003/0063997 A1 | 4/2003 | Fryer |
| 2003/0065292 A1 | 4/2003 | Darouiche |
| 2003/0065297 A1 | 4/2003 | Davis |
| 2003/0071069 A1 | 4/2003 | Shelton |
| 2004/0007000 A1 | 1/2004 | Takeda |
| 2004/0251125 A1 | 12/2004 | Yu |
| 2005/0017380 A1 | 1/2005 | Namespetra |
| 2005/0019237 A1 | 1/2005 | Riley |
| 2005/0168907 A1 | 8/2005 | Sekoguchi |
| 2005/0186108 A1 | 8/2005 | Fields |
| 2005/0220665 A1 | 10/2005 | Ding |
| 2006/0130834 A1 | 6/2006 | Chen |
| 2006/0272682 A1 | 12/2006 | Langford |
| 2007/0031778 A1 | 2/2007 | Helfenbein |
| 2007/0065335 A1 | 3/2007 | Bedard |
| 2008/0050290 A1 | 2/2008 | Yui |
| 2008/0118411 A1 | 5/2008 | D'Arinzo |
| 2009/0080809 A1 | 3/2009 | Pham |
| 2009/0267242 A1 | 10/2009 | Nichols |
| 2010/0047116 A1 | 2/2010 | Garner |
| 2010/0111792 A1 | 5/2010 | Nelson |
| 2010/0112677 A1* | 5/2010 | Onishi ............... A61L 2/202 977/734 |
| 2010/0147302 A1 | 6/2010 | Selvarajan |
| 2011/0031081 A1 | 2/2011 | Iceberg |
| 2012/0164025 A1 | 6/2012 | Stockley, III et al. |
| 2012/0227745 A1 | 9/2012 | Arcilla |
| 2013/0177475 A1 | 7/2013 | Finch |
| 2013/0239994 A1 | 9/2013 | Przyjemski |
| 2014/0112837 A1 | 4/2014 | Huang |
| 2014/0154134 A1 | 6/2014 | Leyva |
| 2015/0004061 A1 | 1/2015 | Kain |
| 2016/0235875 A1 | 8/2016 | Schmidt |
| 2017/0165443 A1 | 6/2017 | Leyva |
| 2017/0202990 A1 | 7/2017 | Leyva |
| 2017/0209610 A1 | 7/2017 | Leyva |
| 2017/0224857 A1 | 8/2017 | Leyva |
| 2017/0225985 A1 | 8/2017 | Leyva |
| 2017/0370013 A1 | 12/2017 | Bahar |

(56) References Cited

U.S. PATENT DOCUMENTS

| | | |
|---|---|---|
| 2018/0028770 A1 | 2/2018 | Parrish |
| 2018/0161466 A1 | 6/2018 | Schmidt |
| 2018/0207307 A1 | 7/2018 | Schwartz |
| 2018/0264157 A1 | 9/2018 | Benedek |
| 2018/0311391 A1 | 11/2018 | Leyva |
| 2018/0311595 A1 | 11/2018 | Leyva |
| 2019/0076561 A1 | 3/2019 | Leyva |
| 2019/0076562 A1 | 3/2019 | Schmidt |
| 2019/0083668 A1 | 3/2019 | Schmidt |
| 2019/0151487 A1 | 5/2019 | Leyva |
| 2019/0167828 A1 | 6/2019 | Leyva |
| 2019/0336627 A1 | 11/2019 | Lucio |
| 2019/0388575 A1 | 12/2019 | Leyva et al. |
| 2020/0000950 A1 | 1/2020 | Bohman |
| 2020/0024167 A1 | 1/2020 | Leyva et al. |
| 2020/0069362 A1 | 3/2020 | Paesch |

FOREIGN PATENT DOCUMENTS

| | | |
|---|---|---|
| CN | 1951507 | 4/2007 |
| CN | 2905066 | 5/2007 |
| CN | 201156965 | 12/2008 |
| CN | 103781498 | 5/2014 |
| CN | 105031693 | 11/2015 |
| CN | 2731632 | 8/2017 |
| CN | 108671253 | 10/2018 |
| EP | 2731632 | 8/2017 |
| JP | S62230601 | 10/1987 |
| JP | H0724064 | 1/1995 |
| JP | 200288091 | 10/2000 |
| JP | 2005270589 | 10/2005 |
| JP | 2009131354 | 6/2009 |
| JP | 2014523327 | 1/2013 |
| KR | 20040098412 | 11/2004 |
| KR | 1020040098412 | 11/2004 |
| KR | 101839063 | 3/2018 |
| WO | 03068274 | 8/2003 |
| WO | 2008116165 | 9/2008 |
| WO | 2011058472 | 5/2011 |
| WO | 2013012696 | 1/2013 |
| WO | 2015171730 | 11/2015 |
| WO | 2017189915 | 11/2017 |
| WO | 2017189916 | 11/2017 |
| WO | 2018200525 | 11/2018 |

OTHER PUBLICATIONS

CPAP Guardian TB-316, America Tyson Industrial Group (Asia Pacific) Limited, http://www.ecvv.com/products/2314441.html, Nov. 91, 2009, downloaded from Internet Jul. 8, 2016, 3 pages.
International Search Report and Written Opinion dated Sep. 17, 2012, issued in PCT Application No. PCT/US12/46593, 6 pages.
International Search Report and Written Opinion dated Jul. 24, 2015, issued in PCT Application No. PCT/US15/29418, 9 pages.
U.S. Office Action dated Jun. 30, 2016, issued in U.S. Appl. No. 15/141,216, 13 pages.
U.S. Office Action dated Jul. 13, 2016, issued in U.S. Appl. No. 15/142,060, 18 pages.
U.S. Office Action dated Jul. 14, 2016, issued in U.S. Appl. No. 15/142,111, 10 pages.
U.S. Office Action dated Jul. 28, 2016, issued in U.S. Appl. No. 15/142,085, 15 pages.
U.S. Office Action dated Oct. 6, 2016, issued in U.S. Appl. No. 15/141,152, 11 pages.
U.S. Office Action dated Nov. 23, 2016, issued in U.S. Appl. No. 15/141,216, 9 pages.
U.S. Office Action dated Nov. 23, 2016, issued in U.S. Appl. No. 15/142,085, 8 pages.
U.S. Office Action dated Feb. 23, 2017, issued in U.S. Appl. No. 29/562,755, 8 pages.
U.S. Office Action dated Feb. 27, 2017, issued in U.S. Appl. No. 29/562,756, 7 pages.

U.S. Office Action dated Mar. 17, 2017, issued in U.S. Appl. No. 15/141,152, 14 pages.
Office Action dated Sep. 21, 2017, issued in U.S. Appl. No. 15/142,085, 9 pages.
Notice of Allowance dated Oct. 13, 2017, issued in U.S. Appl. No. 15/481,919, 7 pages.
U.S. Final Office Action dated Feb. 5, 2018, issued in U.S. Appl. No. 15/141,152, 16 pages.
U.S. Office Action dated Apr. 3, 2018, issued in U.S. Appl. No. 15/873,506, 7 pages.
U.S. Notice of Allowance dated Apr. 27, 2018, issued in U.S. Appl. No. 15/142,085, 8 pages.
International Search Report and Written Opinion dated Jul. 13, 2018, issued in PCT International Patent Application No. PCT/US18/29140, 12 pages.
Office Action dated Aug. 9, 2018, issued in Japanese Patent Application No. 2014-520352, 5 pages. English language translation provided.
Office Action dated Sep. 5, 2018, issued in Chinese Patent Application No. 2016105175158, 10 pages. English language translation provided.
Office Action dated Sep. 17, 2018, issued in U.S. Appl. No. 15/441,929, 10 pages.
Examination Report dated Sep. 26, 2018, issued in Australian Patent Application No. 2017228723, 6 pages.
Preliminary Report on Patentability dated Nov. 8, 2018, issued in PCT International Patent Application No. PCT/US2017/029950, 9 pages.
Office Action dated Jan. 16, 2019, issued in Korean Patent Application No. 10-2018-7009274, 5 pages. English language translation provided.
Notice of Allowance dated Jan. 18, 2019, issued in U.S. Appl. No. 15/441,929, 7 pages.
Office Action dated Jan. 22, 2019, issued in U.S. Appl. No. 16/190,996, 10 pages.
Final Office Action dated Feb. 4, 2019, issued in U.S. Appl. No. 15/141,152, 14 pages.
Office Action dated Mar. 4, 2019, issued in U.S. Appl. No. 15/444,916, 16 pages.
U.S. Appl. No. 16/257,898, filed Jan. 25, 2019.
Examination Report dated May 15, 2019, issued in Australian Patent Application No. 2017228723, 5 pages.
Notice of Allowance dated May 17, 2019, issued in U.S. Appl. No. 16/270,141, 7 pages.
Notice of Allowability dated May 22, 2019, issued in U.S. Appl. No. 15/499,456, 5 pages.
Notice of Allowance dated May 28, 2019, issued in U.S. Appl. No. 15/499,378, 7 pages.
Notice of Allowance dated Jun. 20, 2019, issued in U.S. Appl. No. 16/257,898, 8 pages.
U.S. Office Action dated Jul. 26, 2019, issued in U.S. Appl. No. 16/190,996, 12 pages.
Lenntech "Ozone Generation", Wayback Machine Capture, Mar. 28, 2010, (Year 2010), 3 pages.
Office Action dated Apr. 28, 2019, issued in Chinese Patent Application No. 2017101790491, 10 pages.
Office Action dated Jul. 29, 2019, issued in Chinese Patent Application No. 2017101790472, 8 pages.
Office Action dated Sep. 17, 2019, issued in U.S. Appl. No. 15/444,916, 17 pages.
Preliminary Report on Patentability dated Nov. 7, 2019, issued in PCT Patent Application No. PCT/US2018/029140, 11 pages.
Office Action dated Mar. 23, 2020, issued in Chinese Patent Application No. 2017101790491, 8 pages.
Office Action dated Apr. 15, 2020, issued in U.S. Appl. No. 15/444,916, 16 pages.
ResMed VPAP III ST-A with QuickNav Clinical Guide, copyright 2008 ("ResMed Guide"). Cited by opposing counsel in connection with SoClean Inc. v. Sunset Healthcare Solutions, Inc., Civil action No. 1:20-cv-10351-IT (U.S. Dist. Ct. Massachusetts).
VPAP IV and VPAP IV ST Product Training ("ResMed Presentation"). Cited by opposing counsel in connection with SoClean Inc. v. Sunset Healthcare Solutions, Inc., Civil action No. 1:20-cv-10351-

(56) References Cited

OTHER PUBLICATIONS

IT (U.S. Dist. Ct. Massachusetts). Publication Date is unknown to Applicant, but was asserted by opposing counsel in the noted litigation to be in 2008.
Office Action dated Apr. 28, 2021 in JP 2019-201674, 3 pages.
First Examination Report issued in Indian Patent Application No. 60/MUMNP/2014, dated Jul. 10, 2019, 6 pages.
Office Action dated Nov. 18, 2020 in CN 201780025983.6
Office Action dated May 18, 2021 in CN 201780025983.6
Office Action dated Nov. 1, 2020 in KR 10-2020-7026960.
Office Action dated Jul. 26, 2021, issued in Chinese Patent Application No. 2017101790472, 4 pages.
Office Action dated May 29, 2020, issued in Chinese Patent Application No. 2017101795495, 4 pages.
Office Action dated Jul. 1, 2020, issued in Chinese Patent Application No. 2017101790472.
Office Action dated Jul. 3, 2020, issued in Chinese Patent Application No. 2017101786388, 8 pages.
Restriction Requirement issued in related U.S. Appl. No. 17/025,634, dated Aug. 2, 2021 (6 pages).
Office Action dated May 11, 2021 in BR112018-071444-5.
China Office Action from related matter CN201780025983.6 dated May 9, 2020.
China Office Action from related matter CN201710179459.5 dated May 29, 2020.
International Search Report and Written Opinion from related matter PCT/US20/23631 dated Jun. 3, 2020.
China Office Action from related application CN 201710186091 dated Jul. 1, 2020.
China Office Action from related application CN 20171017904.2 dated Jul. 1, 2020.
U.S. Office Action from related matter U.S. Appl. No. 16/191,059 dated Jun. 11, 2020.
U.S. Final Office Action from related matter U.S. Appl. No. 16/294,097 dated Jun. 11, 2020.
U.S. Office Action from related matter U.S. Appl. No. 15/880,962 dated Jun. 11, 2020.
Office Action dated Jul. 29, 2019, issued in Chinese Patent Application No. 2017101786091, 10 pages.
Office Action dated Jul. 29, 2019, issued in Chinese Patent Application No. 2017101790472.
Office Action dated Aug. 6, 2019, issued in Chinese Patent Application No. 2017101795495, 9 pages.
Notice of Allowance dated Aug. 8, 2019, issued in U.S. Appl. No. 15/141,152, 8 pages.
Examination Report dated Aug. 13, 2019, issued in Australian Patent Application No. 2018200514, 6 pages.
Notice of Acceptance dated Aug. 14, 2019, issued in Australian Patent Application No. 2017228723, 4 pages.
Notice of Allowance dated Oct. 8, 2019, issued in Japanese Application No. 2017-149891, 4 pages.
Examination Report dated Jun. 7, 2019, issued in Canadian Patent Application No. 3,005,981, 3 pages.
Office Action dated Jan. 8, 2021, issued in Chinese Patent Application No. 2017101786388, 8 pages.
Notice of Allowance dated Nov. 15, 2019, issued in Australian Patent Application No. 2018200514, 4 pages.
Extended Search Report dated Nov. 29, 2019, issued in European Patent Application No. 17790471.1, 9 pages.
Examination Report dated Jan. 13, 2020, issued in Chilean Patent Application No. 201803063, 17 pages. English language machine translation included.
Office Action dated Feb. 3, 2020, issued in U.S. Appl. No. 16/190,996, 9 pages.
Office Action dated Feb. 18, 2020, issued in Canadian Patent Application No. 3,005,981, 3 pages.
Office Action dated Mar. 19, 2020, issued in Korean Patent Application No. 10-2020-7003298, 4 pages.
Office Action dated Apr. 7, 2020, issued in U.S. Appl. No. 16/780,492, 13 pages.
Office Action dated Apr. 13, 2020, issued in U.S. Appl. No. 16/782,892, 15 pages.
Notice of Allowance dated Apr. 28, 2020, issued in U.S. Appl. No. 16/780,492, 7 pages.
Office Action dated Apr. 23, 2020, issued in U.S. Appl. No. 16/780,355, 14 pages.
Final Office Action dated Feb. 5, 2019, issued in U.S. Appl. No. 15/141,152, 14 pages.
Examination Report dated Feb. 15, 2019, issued in Australian Patent Application No. 2018200514, 5 pages.
Notice of Allowance dated Apr. 30, 2019, issued in U.S. Appl. No. 15/441,929, 5 pages.
Office Action dated Mar. 4, 2019, issued in U.S. Appl. No. 16/257,898, 13 pages.
Office Action dated Mar. 14, 2019, issued in U.S. Appl. No. 16/270,141, 12 pages.
Notice of Allowance dated Mar. 19, 2019, issued in U.S. Appl. No. 15/499,456, 12 pages.
Extended European Search Report from related Application No. 20773414.6 dated Nov. 17, 2022. 4 pages.
Office Action dated Apr. 2, 2019, issued in Japanese Patent Application No. 2017-0149891, 7 pages.
Office Action dated Oct. 30, 2018, issued in U.S. Appl. No. 15/499,456, 13 pages.
Notice of Allowance dated Oct. 31, 2018, issued in U.S. Appl. No. 15/873,506, 8 pages.
Office Action amendment dated Oct. 31, 2018, issued in U.S. Appl. No. 15/499,456, 13 pages.
Office Action dated Nov. 6, 2018, issued in U.S. Appl. No. 15/499,378, 18 pages.
Preliminary Report on Patentability dated Nov. 8, 2018, issued in PCT International Patent Application No. PCT/US2017/029949, 9 pages.
Chaunet et al., "The Sterilization Technology for the 21st Century", TS03, Inc. Québec, Canada, 2007.
Office Action dated Oct. 20, 2021 in U.S. Appl. No. 17/025,634. 9 pages.
Goodknight 420G Patient Manual, 2005, Nellcor Puritan Bennett Inc., pp. i-vi; pp. 1-23.
Office Action dated May 10, 2021, issued in Indian Patent Application No. 201827043772, 8 pages.
SoClean 2 PAP Disinfecting Device User Guide Copyright 2011-2014, Inceptus, Inc.
Ohkawa et al. "High grade disinfection using high-density ozone," J Adv Oxid Tech, 7, 154-160, (2004).
International Search Report and Written Opinion dated Aug. 16, 2017, issued in PCT Patent Application No. PCT/US17/29950, 11 pages.
U.S. Office Action dated Aug. 3, 2017, issued in U.S. Appl. No. 15/141,152, 14 pages.
International Search Report and Written Opinion dated Aug. 2, 2017, issued in PCT Patent Application No. PCT/US17/29949, 11 pages.
U.S. Office Action dated Jun. 13, 2017, issued in U.S. Appl. No. 15/481,919, 10 pages.
Keep your CPAP machine clean and safe, Oct. 18, 2010—Available at https://www.cpap.co.uk/2010/10/keep-your-cpap-machine-clean-and-safe.
GoodKnight H20 Heated Humidifier User's Manual, 2006 Nellcor Puritan Bennett Inc., pp. i-iv and 1-16.
Hoffrichter Trend II User's Manual (date unknown), Germany, pp. 1-79.
Hudson RCI Product Catalog (2004-2005).
KnightStar(R) 330 User's Manual, 2006, Nellcor Puritan Bennett, 68 pages.
DeVilbiss@ DV54 AutoAdjust CPAP Series (DeVilbiss® SleepCube Positive Airway Pressure Device) User Manual (2009). Available at https://www.manualslib.com/manual/1577762/Devilbiss-Intellipap-Dv54.html, pp. 1-183.
Sunset Healthcare Solutions, Inc's Preliminary Patent Disclosures Pursuant to Local Rule 16.6(d)(4) in *SoClean, Inc.* v. *Sunset Healthcare Solutions, Inc*, in Civil Action No. 1:20-cv-10351-IT.

(56) References Cited

OTHER PUBLICATIONS

Sunset Healthcare Solutions, Inc's Second Amended Counterclaims in *SoClean, Inc.* v. *Sunset Healthcare Solutions, Inc*, in Civil Action No. 1:20-cv-10351-IT and Consolidated Case No. 1:21-cv-1013IT.
Memorandum in Support of SoClean's Motion to Dismiss Counts Eight and Nine of Sunset's Second Amended Counterclaims, *SoClean, Inc.* v. *Sunset Healthcare Solutions, Inc*, in Civil Action No. 1:20-cv-10351-IT and Consolidated Case No. 1:21-cv-1013IT.
Defendant Sunset's Memorandum in Opposition to SoClean's Motion to Dismiss Counts Eight and Nine of Sunset's Second Amended Counterclaims. C.A. No.: 1:20-cv-10351-IT. Filed Jul. 23, 2021, 165 pages.
9055 Series DeVilbiss RPM Bilevel CPAP System Instruction Manual, 66 pages.
Al Ashry, et al. "Humidification during Mechanical Ventilation in the Adult Patient", vol. 2014, Article ID 715434, Hindawi Publishing Corporation, BioMed Research International. 12 pages.
Murphy, "Ozone—The Latest Advance in Sterilization of Medical Developments", Canadian Operating Room Nursing Journal, vol. 24, No. 2, Jun. 2006, pp. 28, 30-32, 37 and 38.
Ishizaki, et al., "Inactivation of Bacillus Spores by Gaseous Ozone", Journal of Applied Bacteriology, 1986, 60, 67-72,.
Tornado, New Kind of CPAP Guardian, User Manual, Sunset, 8 pages.

\* cited by examiner

TECHNOLOGIES FOR SANITIZING MIST HUMIDIFIERS

FIELD

The present disclosure generally relates to technologies for sanitizing a mist humidifier and, in particular, the reservoir of a mist humidifier. Aspects of the present disclosure therefore relate to devices and systems for sanitizing a mist humidifier and, in particular, the reservoir thereof. Methods of sanitizing a mist humidifier are also disclosed.

BACKGROUND

Many humidifiers have a reservoir that includes one or more mist channels that are connected to one or more mist release openings. For example, cool and warm mist humidifiers may include such a reservoir. In such instances the reservoir is generally configured to release a mist of a liquid contained therein from the mist release opening(s). Similarly, other types of reservoirs may include mist release openings.

Liquid reservoirs such as those used in a mist humidifiers may become fouled with bacteria, mold and other contaminants. In particular, many mist humidifiers have issues with mold and bacterial growth on various parts of the reservoir, such as but not limited to the bottom tray, sidewalls, and mist passageways. Mold, bacteria, and other contaminants may also build up within water in the reservoir of a mist humidifier, particularly when the water has been stagnant for an extended period. Periodic cleaning and/or sterilization of such reservoirs may therefore be desired to help ensure that the humidifier is sanitary and safe for use.

With the foregoing in mind, many liquid reservoirs for mist humidifiers are infrequently cleaned and/or sanitized by users. Additionally, many commonly recommended methods for cleaning mist humidifiers can be messy, time consuming, and inconvenient. For example, the user guide of some mist humidifiers may recommend cleaning the reservoir and/or other components of the machine using a cleaning solution that is a mixture of water and vinegar. Such methods can be inconvenient, as they often require the user to prepare the cleaning solution themselves. A cleaning solution of water and vinegar may also not effectively kill some types of water born mold and/or bacteria, and therefore may inadequately sanitize the reservoir of a mist humidifier.

Other commonly recommended methods of cleaning a mist humidifier include manual washing, scrubbing, and drying of the reservoir. Such methods are often time consuming and considered to be undesirable to consumers. Moreover because many parts of a reservoir for a mist humidifier are difficult to reach, they are also difficult to clean using traditional methods such as manual washing and scrubbing.

Accordingly the inventors have identified that there is a continued interest in the development of novel devices, systems, and methods for sanitizing all or a portion of a mist humidifier, including but not limited to the water reservoir thereof.

BRIEF DESCRIPTION OF THE DRAWINGS

Reference is now made to the following detailed description which should be read in conjunction with the following figures, wherein like numerals represent like parts.

DETAILED DESCRIPTION

Figure 1:
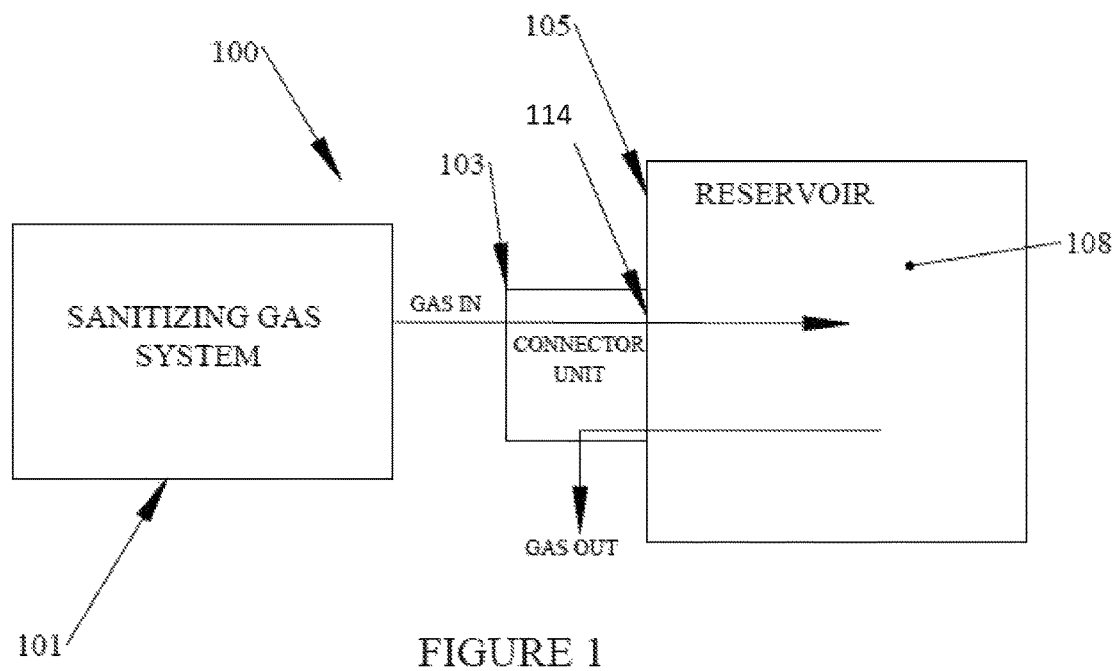
FIG. 1 is a block diagram illustrating a sanitizing gas flow between a reservoir sanitization system and a reservoir, consistent with the present disclosure.

As explained in the background, various methods are known for cleaning humidifiers, (and in particular mist humidifiers). Such methods, however, can be inconvenient, messy, time-consuming, etc., and therefore may be rarely performed by consumers. They methods may also result in inadequate sanitization of a mist humidifier, and in particular the reservoir thereof and any water therein. The inventors have therefore identified that there is a need in the art for technologies (e.g., devices, systems and methods) that enable convenient, easy and effective sanitization of a mist humidifier and, in particular, the reservoir of a mist humidifier and any water therein.

With the foregoing in mind, aspects of the present disclosure relate to devices, systems and methods that utilize a sanitizing gas to sanitize all or a portion of a mist humidifier, such as but not limited to a reservoir thereof. As will be described in detail later, the devices, systems and methods of the present disclosure are particularly useful for sanitizing the bottom tray, mist channel and the reservoir of a mist humidifier. The technologies described herein are not limited to such applications, however, and can be utilized to sanitize a type of reservoir, such as those that may be used in soda fountains, animal watering machines, for bottle sanitization and the like.

Although the technologies described herein can be used with many sanitizing gases, the present disclosure focuses on the use of ozone as a sanitizing gas. This is because ozone ($O_3$) gas is an effective sanitizer, yet is relatively safe for consumer use. Indeed because of its strong oxidizing properties, ozone can effectively kill or otherwise remove a wide range of organic and inorganic contaminants such as yeasts, bacteria, molds, viruses, other pathogens, and/or pollutants with which it comes into contact, e.g., via oxidation. Yet naturally over time and/or as it oxidizes contaminants, ozone may be chemically reduced to oxygen ($O_2$), which is safe for human consumption and for release into the environment. Ozone is also relatively easy to generate on site (and thus does not require the use of a storage tank), and leaves little or no chemical residue. For those and other reasons, ozone has been identified as a safe and effective sanitizing gas for use in the present disclosure. It should be understood, however, that the technologies described herein are not limited to the use of ozone, and may be employed with a wide variety of sanitizing gases.

Also for the sake of illustration, the present disclosure focuses on embodiments in which the technologies described herein are employed to sanitize a bottom tray and/or a water reservoir of a mist humidifier. It should be understood that such examples are for the sake of illustration only, and that the technologies described herein may be used to sanitize a wide variety of reservoirs that may be used in applications other than a humidifier.

As used herein, the term "mist humidifier" refers to any of a wide variety of devices or machines that may be utilized to disperse a mist of a liquid into the air proximate the mist humidifier.

As used herein, the term "fluidly coupled" means that two or more components are connected to one another such that a gas may be conveyed between them. In contrast, the term "coupled" when used alone means that two or more components are connected to one another chemically (e.g., via an adhesive), mechanically (e.g., via fasteners, mechanical interference, etc.), or by other means.

One aspect of the present disclosure relates to systems for sanitizing a mist humidifier and, in particular a bottom tray and/or a reservoir of a mist humidifier. As will be described further below, the systems described herein generally include a gas supply system, a connector unit, and an exhaust system. The connector unit is configured to be installed within an opening in a portion of a humidifier, such as but not limited to the top of a mist chamber, to an opening in a cover, or to an opening in a sidewall, cover, or bottom thereof. The connector unit includes an inlet passageway for the introduction of a sanitizing gas into the reservoir, and an outlet passageway for the removal of sanitizing gas from the reservoir.

The connector unit is configured such that when it is so installed, it spans across the opening in the humidifier. In addition, the connector unit is configured to control the flow of gases into and out of the reservoir. For example, in some embodiments the connector unit may be configured to control the introduction of gas (e.g., sanitizing gas) into the reservoir, and to control the release of gas (e.g., sanitizing gas) from the reservoir. In embodiments, the connector unit includes a flexible grommet that is configured to fit within the opening in the reservoir and to connect with the inner radial surface of the opening. In embodiments, the grommet may form a liquid and/or gas tight seal between the connector unit and the inner surface of the opening.

The gas supply system of the sanitization systems described herein is generally configured to generate a sanitizing gas, such as but not limited to ozone. A proximal end of a distribution line may be coupled to the gas supply system, such that sanitizing gas generated by the gas supply system can be received therein. In embodiments, the supply line may extend through an inlet passageway in the connector unit, such that the distal end of the supply line is disposed within the reservoir (and optionally below a surface of any liquid in the reservoir). Alternatively, the supply line may be a first supply line having a proximal end coupled to the gas supply system, and a distal end fluidly coupled to the proximal end of the inlet passageway, e.g., via an inlet connector. In such instances a second supply line may have a proximal end fluidly coupled to a distal end of the inlet passageway, and a distal end disposed within the reservoir (and optionally below a surface of any liquid therein).

In operation, the gas supply system may generate a sanitizing gas. The sanitizing gas may be conveyed into the distribution line(s), through the inlet passageway of the connector unit (directly or via a distribution line) and into a portion of the humidifier, such as the reservoir, bottom tray, and/or mist chamber thereof. The locations to which the sanitizing gas is conveyed in the humidifier depend on the humidifier, the location of the opening in the humidifier, and/or placement of the distal end of the (e.g., second) distribution line.

The exhaust system may be separate from or integral with the connector unit. In embodiments, the exhaust system is integral with the connector unit. For example, the exhaust system may be included within the connector unit, such that it covers a portion of an opening into the humidifier, such as an opening in the humidifier reservoir. In any case, the exhaust system may include a filter that is configured to remove or convert excess sanitizing gas into another composition prior to its release into the environment. For example, a sanitizing gas (e.g., ozone) may be introduced into a reservoir of a humidifier through an inlet passageway of a connector unit, as previously described. The sanitizing gas may sanitize the interior of the reservoir and any liquid therein, as well as other components that may be fluidly coupled to the reservoir (e.g., a mist chamber). Excess sanitizing gas within the reservoir (or other components of the humidifier) may rise or be drawn into the exhaust system (e.g., via a pump), where it may contact a filter therein. The filter may absorb the excess sanitizing gas or convert it into a composition that is safe for human inhalation and/or release into the environment. For example when the sanitizing gas is ozone, the filter in the exhaust system may absorb the ozone and/or convert it to oxygen.

Figure 1A:
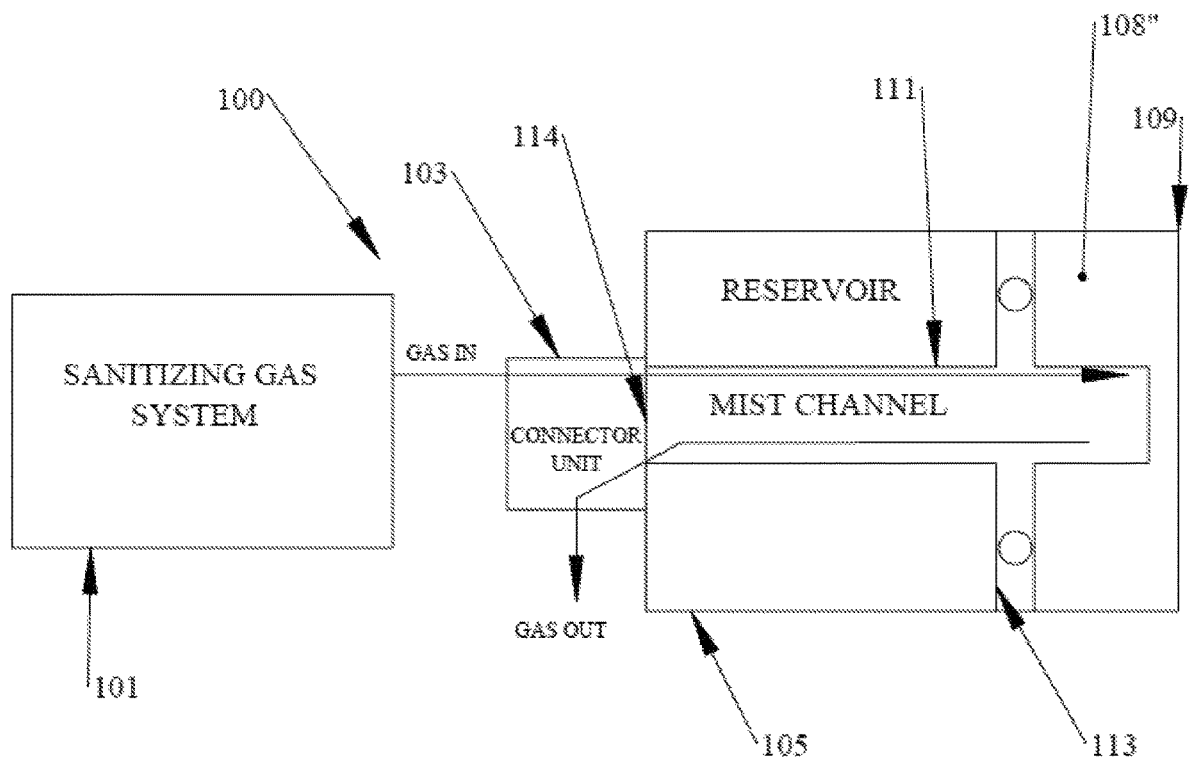
FIG. 1A is a block diagram illustrating a sanitizing gas flow between a reservoir sanitization system via a mist channel to a bottom tray of a reservoir, consistent with the present disclosure.

FIGS. 1 and 1A are block diagrams illustrating the flow of sanitizing gas between a humidifier sanitization system consistent with the present disclosure and a reservoir of a humidifier. As shown, the humidifier sanitization system 100 includes a sanitizing gas system 101 and a connector unit 103. The sanitizing gas system 101 is fluidly coupled to the connector unit 103 such that it can provide a gas inflow (gas in) to the connector unit 103. The connector unit 103 is fluidly coupled to the reservoir 105 of the humidifier via an opening 114, and includes an inlet passageway 115. In embodiments, a flexible grommet extends radially around the opening in the reservoir, and is configured to form a liquid and/or gas tight seal between the connector unit 103 and a surface of the opening. In the embodiment of FIG. 1A, the opening 114 in the reservoir may be fluidly coupled to a mist channel 111 of the humidifier, as further described below.

The reservoir 105 may or may not include a liquid (e.g., water). For the sake of illustration, the reservoir 105 is shown in FIGS. 1 and 1A without liquid. The sanitizing gas system 101 is configured to generate a sanitizing gas (e.g., ozone), and to supply an inflow of the sanitizing gas (gas in) to the connector unit 103. The inflow of sanitizing gas passes through the connector unit 103, into the reservoir 105. In embodiments where water or another liquid is contained in the reservoir 105, the connector unit and/or a distribution line) may be configured to deliver the sanitizing gas below a surface of such liquid.

The sanitizing gas supplied by the gas inflow may sanitize the interior of the reservoir, including any liquid in the reservoir, the bottom and sidewalls of the reservoir, the air 108 in the reservoir etc, as well as portions of the reservoir 105 that are below the level of the liquid 107, including the bottom tray 109 of the humidifier. When liquid is included in the reservoir, the sanitizing gas may be introduced into the liquid. A portion of the sanitizing gas so introduced may sanitize the liquid. In addition, a portion of the sanitizing gas supplied by the gas inflow may evolve from the liquid into the air 108 within the reservoir 105 and/or air 108" within a mist channel 111 as shown in FIG. 1A. In either case the sanitizing gas may sanitizing the air 108, 108".

Excess sanitizing gas within the humidifier 105 may be converted to another composition and/or be removed from the interior of the humidifier 105 including the reservoir 105 and the mist chamber 111 via an exhaust system included in the connector unit 103. More specifically, excess sanitizing gas may be conveyed via the air 108 in the reservoir and/or the air 108" in the mist channel 111 to an outlet passageway into the connector unit 103. In embodiments, a pump (included in the connector unit 103 or separate therefrom) may be used to draw excess sanitizing gas into the outlet passageway. A filter may be disposed within the outlet passageway. When used, the filter may be configured to absorb the sanitizing gas and/or to convert the sanitizing gas to another composition that is safe for discharge into the environment. Non-limiting examples of suitable filters that may be used for such a purpose include magnesium oxide filters and activated carbon filters.

Figure 2:
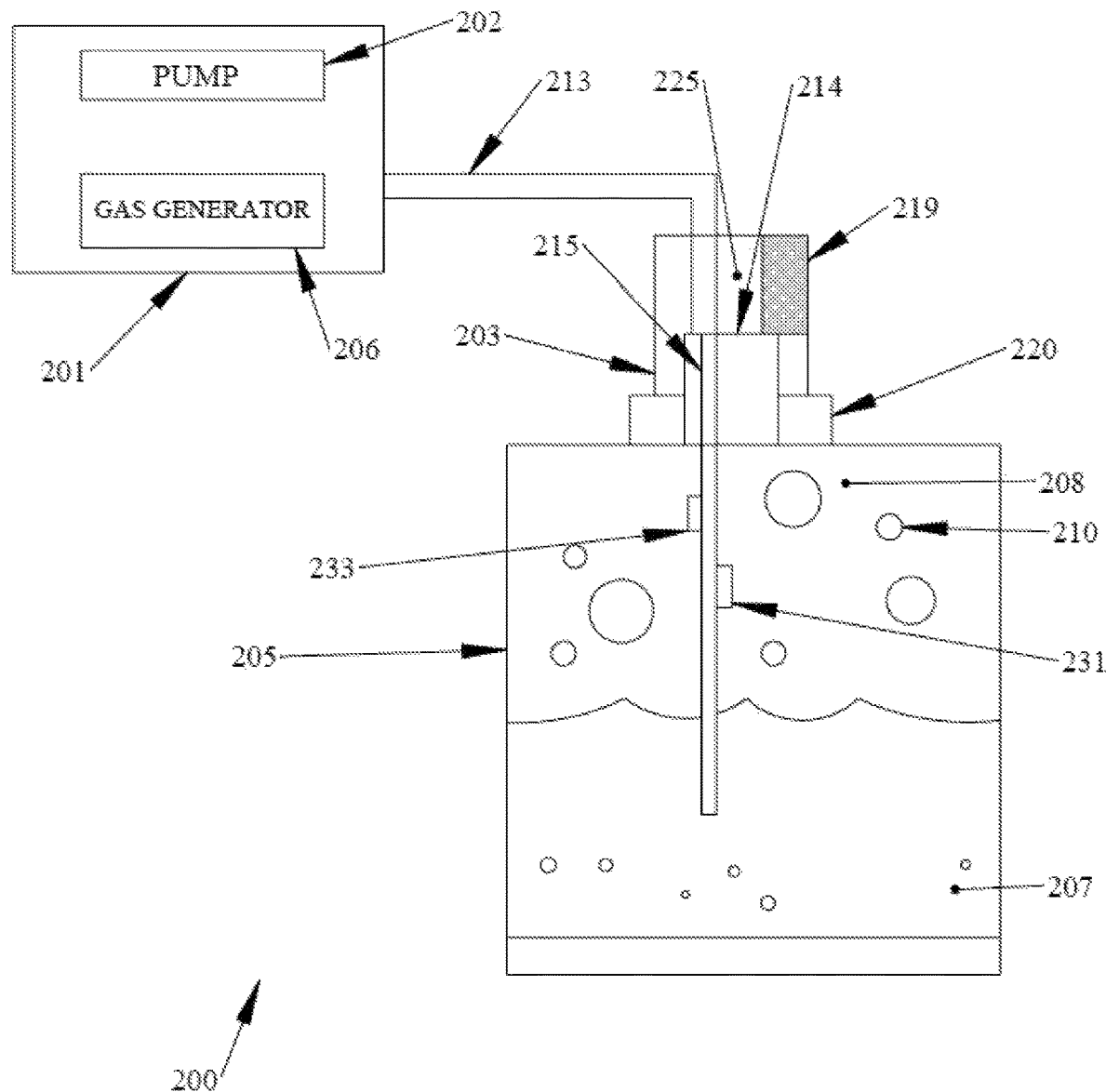
FIG. 2 illustrates an example reservoir sanitization system including a connector unit and a supply line consistent with the present disclosure.
Figure 2A:
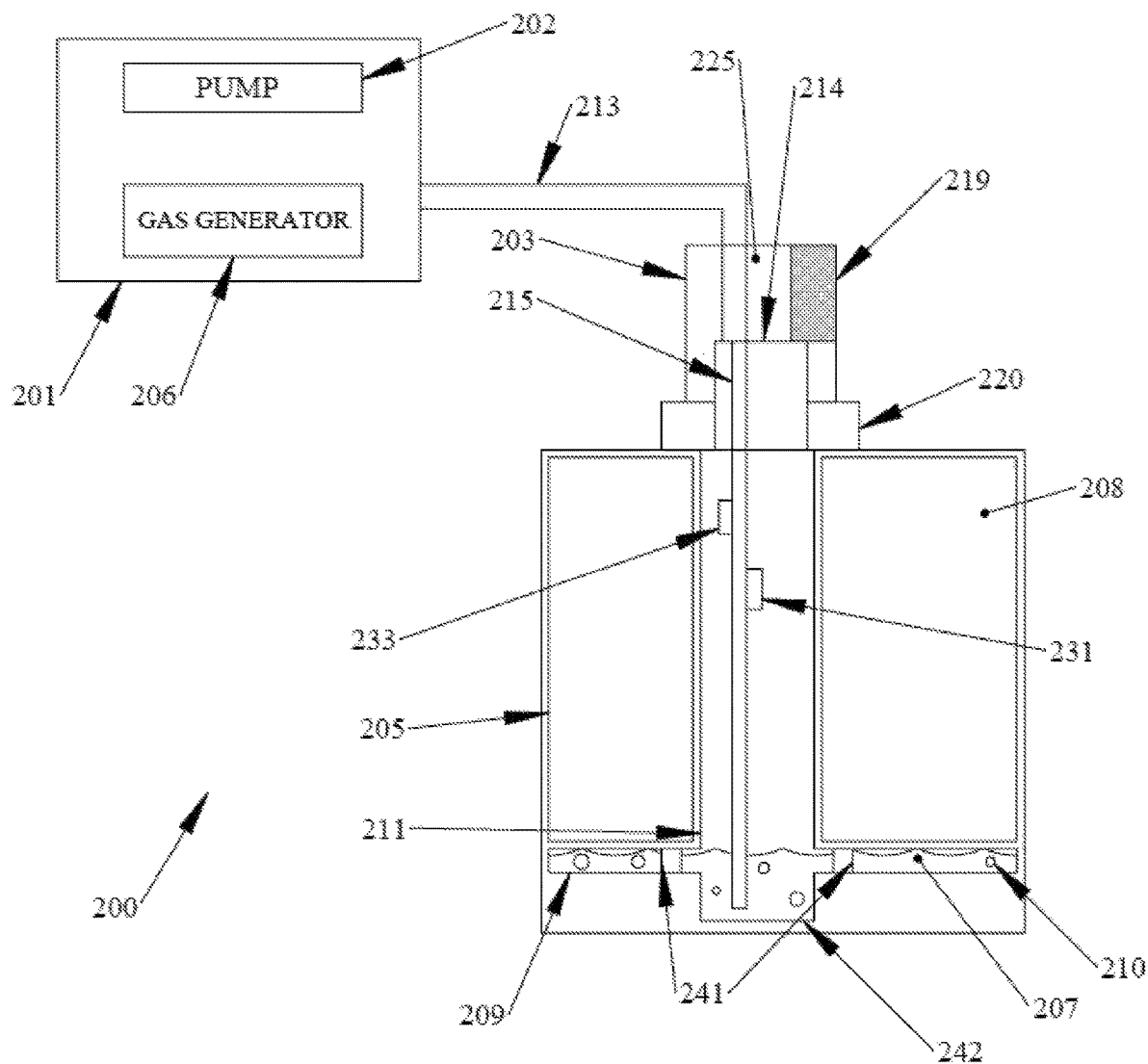
FIG. 2A illustrates another example reservoir sanitization system including a connector unit and a supply line consistent with the present disclosure.

FIGS. 2 and 2A are block diagrams depicting two examples of a humidifier sanitization system 200 consistent with the present disclosure, and which for the sake of example are illustrated as installed within a reservoir 205 that does (FIG. 2A) or does not (FIG. 2) include a mist channel. As shown, the humidifier sanitization system includes a sanitizing gas system 201 that is fluidly coupled to a connector unit 203. In these embodiments, the sanitizing gas system 201 includes a pump 202 and a gas generator 206. The pump 202 (e.g., an air pump) is configured to generate a flow of air and the gas generator 206 is configured to generate a sanitizing gas 210, such as but not limited to ozone.

The connector unit 203 includes an inlet passageway 215 that occupies a portion of the opening 214. And outlet passageway is formed by another portion of the opening, and is fluidly coupled to an exhaust system 225. The exhaust system 225 includes a filter 219 for absorbing and/or converting sanitizing gas to another composition. The inlet passageway 215 is configured to allow a supply line 213 to pass there through, such that a distal end of the supply line 213 is disposed within reservoir 205, such as within a liquid 207 that is within the reservoir (FIG. 2) or a bottom tray (FIG. 2A). Consistent with the prior description, the connector unit 203 is generally configured to be installed in or around an opening 214 of the humidification device, which may be located in a wall, bottom, top, cover or cover extension of the humidification device 200.

For the sake of illustration, the opening 214 in FIGS. 2 and 2A is depicted as being part of an outlet port of humidifier, which may be in fluid communication with a reservoir 205 or a mist channel 211, as shown in FIGS. 2 and 2A, respectively. In those embodiments when the connector unit 203 is installed it may span across the opening 214, as shown in both FIGS. 2 and 2A.

The humidifier sanitization system may further include a sealing system 220. In general, the sealing system 220 may function to provide or facilitate the formation of a gas-tight seal between the connector unit 203 and the opening 214. In embodiments, the sealing system 220 may include a self-sealing grommet, a press-fit seal, a clip-seal, or another suitable device that is configured to couple around the opening 214 or around an opening extension (e.g., tube, lid, etc.). Of course such examples are not limiting, and any suitable sealing system may be used provided it can provide or form a gas tight seal between the opening 214 and the connector unit 203.

In FIGS. 2 and 2A the supply line 213 passes through the inlet passageway 215 in the connector unit 203, such that a distal end thereof is disposed within the interior of the humidification device 200. The distal end of the supply line 213 may be immersed below any liquid 207 in the reservoir 205 (as shown in FIG. 2) or immersed below the surface of any liquid 207 in the bottom tray 209 (as shown in FIG. 2A). In such embodiments the sanitizing gas 210 may be released below the surfaced of the liquid 207 in the reservoir (FIG. 2) or the bottom tray 209 (FIG. 2A).

As shown in the embodiment of FIG. 2A the humidifier may further include a mist connector 211, a bottom tray 209 and liquid 207 (e.g. water) in the bottom tray 209. Valve extensions 241 on the bottom tray 209 may reach valves in the reservoir 205, so as to facilitate the release droplets of liquid into a liquid compartment 242 below the mist channel 211. In such instances the line 213 is configured to extend down the mist channel 211 into the compartment 242, and into any liquid 207 therein.

As discussed above an exhaust system 225 is integral with or removably coupled to the connector unit 203. In some embodiments, the exhaust system 225 is disposed within or above a portion of the opening 214. In any case, the exhaust system 225 is fluidly coupled to the opening 214. Sanitizing gas drawn from the humidifier via the opening 214 may come into contact with a filter contained in the exhaust system 225 and/or disposed within an open portion of the opening 214. As discussed previously, the filter is configured to absorb the sanitizing gas or convert it to another composition.

As further shown in FIGS. 2 and 2A, an optional check valve 231 may be provided on a distal portion of supply line 213. When used, the optional check valve 231 is generally configured to prevent a backflow of liquid 207 into the supply line 213. An optional sensor 233 may also be provided to sense a presence and/or concentration of sanitizing gas (e.g. ozone gas) within the interior of humidifier 200 and/or within connector unit 203. In some embodiments the sensor 233 (when used) may be configured to provide a signal to a user interface, wherein the signal causes the user interface to indicate whether or not a safe level of the sanitizing gas is present in the humidifier 200, and/or to indicate when a mist humidifier including the reservoir 205 is safe to use.

Figure 3:
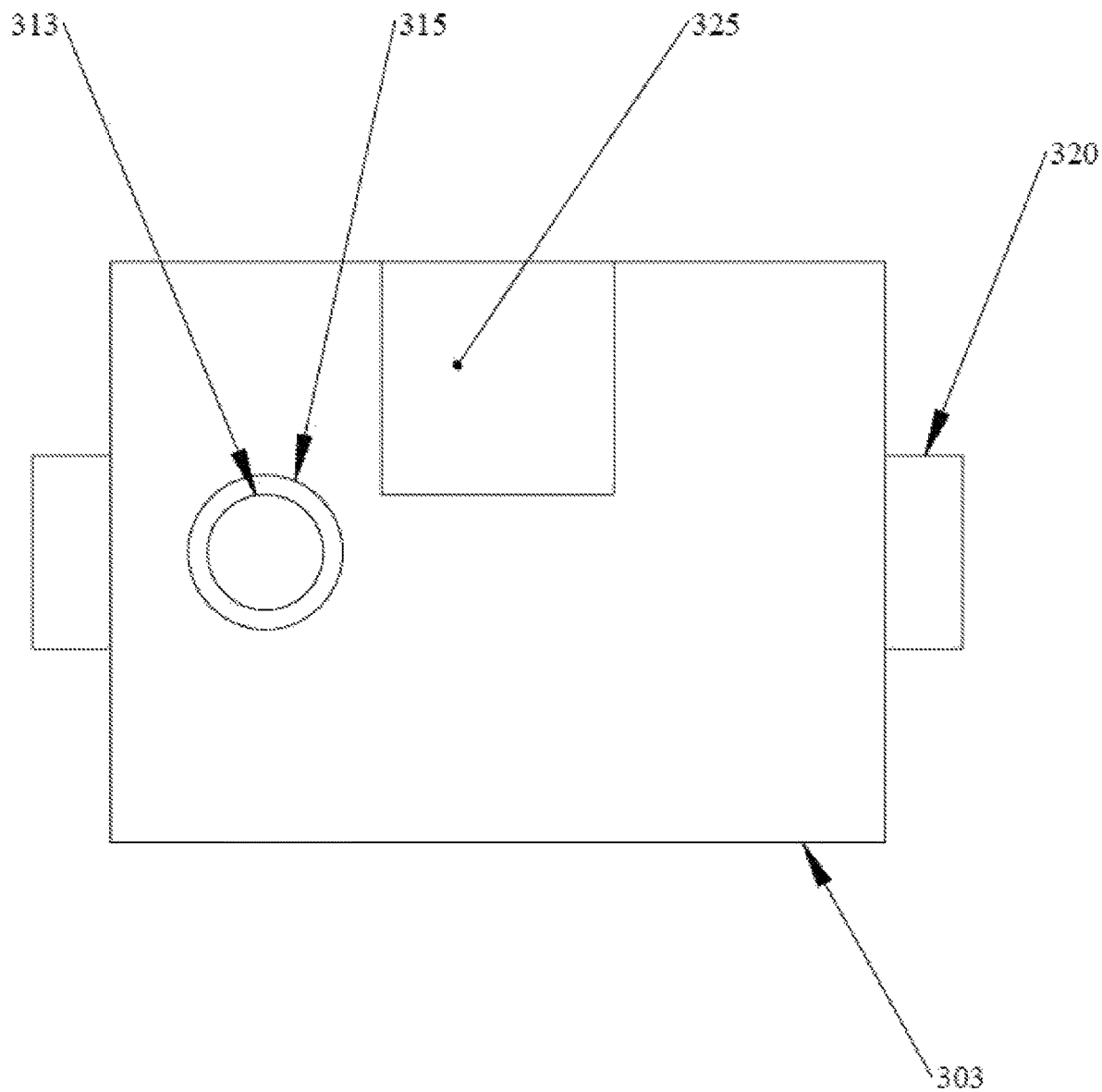
FIG. 3 is a top view of one example of a connector unit consistent with the present disclosure.

FIG. 3 is a top view of one example of a connector unit consistent with the present disclosure. As shown, the connector unit 303 includes an inlet passageway 315 for the passage of a supply line 313 therethrough. An exhaust system 325 and an optional sealing system 320 are integral with or coupled to the connector unit 303. The function of the exhaust system is the same as exhaust systems 125, 225, and therefore is not described again. The connector unit 303 once installed connects to an opening in the humidifier 300 such that the inlet passageway 315 and the exhaust system 322 are fluidly connected with a mist passageway or opening in a humidifier.

Figure 4:
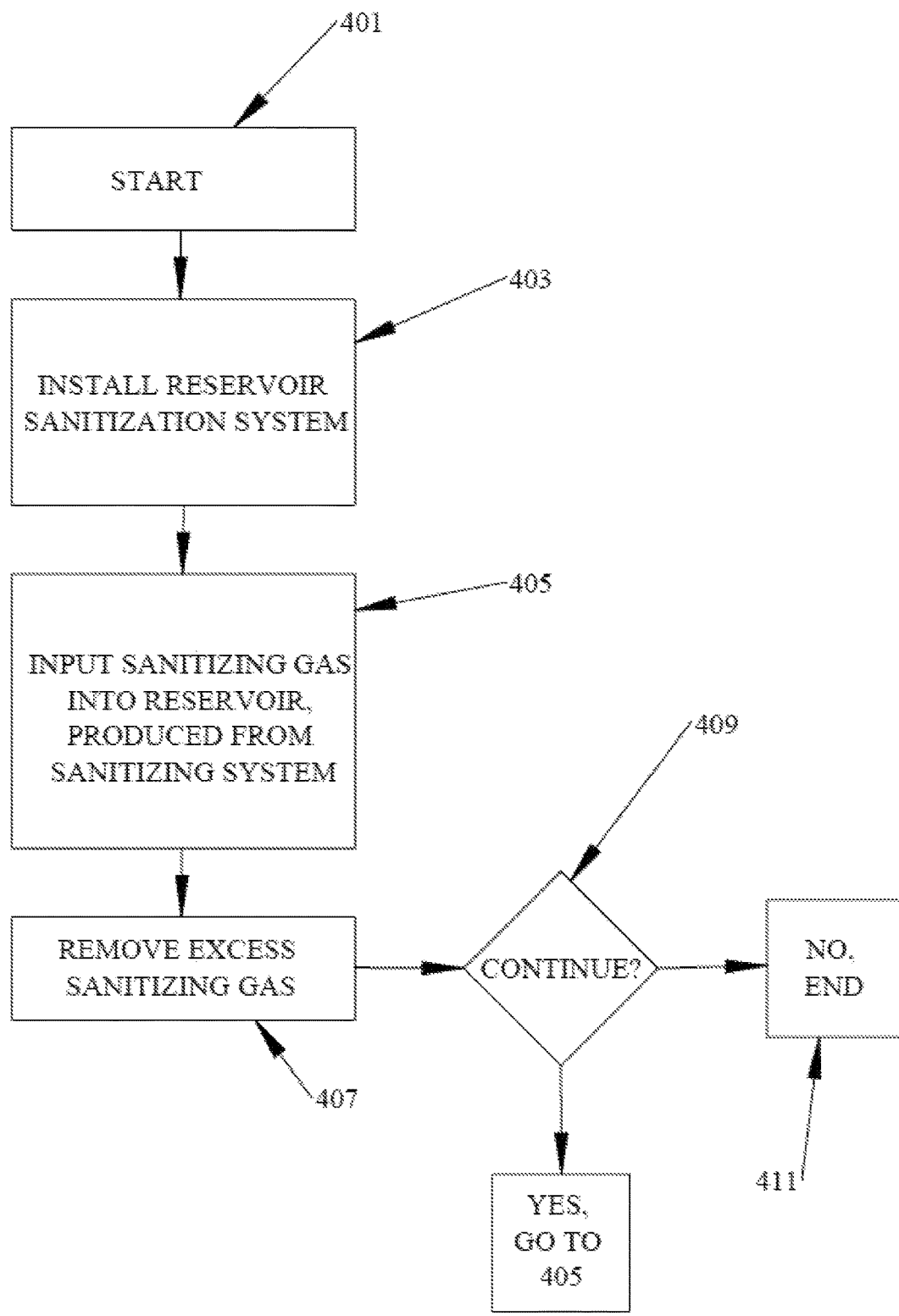
FIG. 4 is a flow chart of example operations of a reservoir sanitization method consistent with the present disclosure.

Another aspect of the present disclosure relates to methods for sanitizing a humidifier with a reservoir. In that regard reference is made to FIG. 4, which is a flow chart of example operations of one example of a reservoir sanitization method consistent with the present disclosure. As shown, the method 400 begins at block 401. The method may then advance to optional block 403, pursuant to which reservoir sanitization system with the present disclosure may be installed, for example to an opening in the humidifier above the reservoir or above the mist chamber.

Following the operations of block 403 or if block 403 is omitted (e.g. where a reservoir sanitization system is already installed in a reservoir), the method may proceed to block 405. Pursuant to block 405 a sanitizing gas may be provided into a humidifier via a supply line e.g., as described above. Operations pursuant to block 405 may include, for example, generating a sanitizing gas with a gas generator, causing the sanitizing gas to flow into a supply line and into a reservoir or through a mist chamber, as previously described. At least a portion of the sanitizing gas so provided may sanitize the interior of the reservoir, including any liquid (e.g., water therein).

The method may then advance to block 407, pursuant to which excess sanitizing gas may be removed from the interior of the humidifier. Consistent with the foregoing description, operations pursuant to block 407 may include drawing sanitizing gas from the interior of the reservoir into an exhaust system. The operations pursuant to block 407 may also include conveying the sanitizing gas to a filter, as discussed above.

Following the operations of block 407 the method may proceed to block 409, pursuant to which a decision may be made as to whether the method is to continue. The outcome of the decision block 409 may be contingent on a sensor signal provided, e.g., by an optional sensor or on some other criteria. In any case if the method is to continue it may loop back to block 405, but if not, the method may proceed to block 411 and end.

The following examples pertain to additional non-limiting embodiments of the present disclosure.

EXAMPLES

Example 1: According to this example there is provided a system for sanitizing a humidifier with a reservoir, including: a sanitization system including a pump and a gas generator, the sanitization system configured to supply a sanitizing gas, a connector unit configured to removably couple with an opening in the humidifier that is used to release a mist of a liquid when the humidifier is in operation, the connector unit including an inlet passageway configured to extend into at least a portion of the opening; a supply line configured to fluidly couple the gas generator to an interior of the reservoir, wherein the supply line passes through the inlet passageway; and an exhaust system removably coupled to the connector unit and configured to fluidly couple with a portion of the opening, the exhaust system further configured to remove the sanitizing gas from the reservoir.

Example 2: This example includes any or all of the features of example 1, wherein the exhaust system further includes a removable filter.

Example 3: This example includes any or all of the features of example 1, wherein a distal end of the supply line is configured to be disposed within a mist chamber of the humidifier.

Example 4: This example includes any or all of the features of 1, and further includes a check valve coupled to the supply line.

Example 5: This example includes any or all of the features of 1, and further includes a sensor for sensing sanitization gas in the humidifier.

Example 6: This example includes any or all of the features of example 1, and further includes a display for notifying a user with safe-use instructions.

Example 7: According to this example there is provided a system for sanitizing a humidifier with a reservoir, including: a connector unit configured to removably and fluidly couple with an opening in the humidifier; and a self-sealing flexible grommet that is configured to provide a gas tight seal between a surface defining the opening and the connector unit; and an exhaust system wherein: the connector unit includes an inlet passageway that is configured to extend through a portion of the opening and to fluidly couple to a sanitizing gas generator; the exhaust system is removably coupled to the connector unit such that it is disposed over at least a portion of the opening when the connector unit is installed, the exhaust system configured to drawn sanitizing gas from the reservoir.

Example 8: This example includes any or all of the features of example 7 wherein the exhaust system further includes a removable filter.

Example 9: This example includes any or all of the features of example 8 wherein the removable filter is a removable magnesium oxide filter.

Example 10: This example includes any or all of the features of example 7, and further includes a supply line, wherein at least a portion of the supply line extends through the inlet passageway.

Example 11: This example includes any or all of the features of example 7 and further includes a sensor for sensing sanitization gas in the reservoir.

Example 12: This example includes any or all of the features of example 7 and further includes a display.

Example 13: According to this example there is provided a system for sanitizing a humidifier with a reservoir including: a sanitization system including a pump and a gas generator, the sanitization system configured to supply a sanitizing gas; a connector unit, the connector unit configured to removably couple with an opening in the humidifier, the connector unit including an inlet passageway configured to extend through at least a portion of the opening; a sealing system configured to provide a gas tight seal between a surface defining the opening and the connector unit; a supply line including a proximal end and a distal end, the proximal end fluidly coupled to the sanitizing gas system to receive the sanitizing gas; and an exhaust system; wherein: the supply line is configured to extend through the inlet passageway and through a mist passageway in the humidifier, such that the distal end of the supply line is disposed proximate a bottom tray of the humidifier; and the exhaust system configured to remove the sanitizing gas.

Example 14: This example includes any or all of the features of example 13, wherein the exhaust system further includes a removable filter.

Example 15: This example includes any or all of the features of example 14, wherein the removable filter is a removable magnesium oxide filter.

Example 16: This example includes any or all of the features of example 13, and further includes a check valve coupled to the supply line.

Example 17: This example includes any or all of the features of example 13, and further includes a sensor for sensing sanitization gas in the water reservoir.

Example 18: This example includes any or all of the features of example 13, and further includes a display.

Example 19: According to this example there is provided a method for sanitizing a humidifier with a reservoir, including: coupling a connector unit to an opening in the humidifier that is used to release a mist of a liquid when the humidifier is in operation, the connector unit including an inlet passageway configured to extend through at least a portion of the opening and an exhaust system detachably coupled thereto; inputting sanitizing gas into the humidifier via supply line extending through the inlet passageway into the humidifier, the supply line including a proximal end coupled to a sanitizing gas generator; and exhausting sanitizing gas from the humidifier.

Example 20: This example includes any or all of the features of example 19, and further includes installing a sealing system into the opening prior to coupling the connector unit.

Example 21: This example includes any or all of the features of example 20, wherein the sealing system is a flexible grommet.

Example 22: According to this example there is provided a connector unit for sanitizing a humidifier, including: a body; an inlet passageway configured to extend through at least a portion of an opening in the humidifier that is used to supply a mist when the humidifier is in operation, wherein the inlet passageway is configured to receive at least a portion of a supply line; an exhaust system detachably coupled to the body, the exhaust system configured to be disposed over and an fluid communication with at least a portion of the opening when the connector unit is installed therein; and a sealing system, the sealing system configured to provide a gas tight seal between a portion of the body and a surface of the opening.

Example 23: This example includes any or all of the features of example 22, wherein the exhaust system further includes a filter.

Example 24: This example includes any or all of the features of example 23, wherein the filter is a magnesium oxide filter.

Example 25: This example includes any or all of the features of example 22, wherein the sealing system is a flexible grommet.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

What is claimed is:

1. A system, comprising:
   a humidifier comprising a reservoir comprising an opening, and a mist channel fluidly coupled to the opening; and
   a connector unit fluidly coupled with the opening, the connector unit comprising an inlet passageway and an outlet passageway;
   a sanitization system comprising a pump and a gas generator, wherein the gas generator is fluidly coupled to the inlet passageway;
   wherein when the system is in operation:
   sanitizing gas flows from the sanitization system, through the inlet passageway, and into an interior of the humidifier; and
   sanitizing gas flows from the interior of the humidifier, through the mist channel, and through the outlet passageway.

2. The system of claim 1, further comprising a supply line, wherein the supply line fluidly couples the gas generator to the interior of the reservoir and passes through the inlet passageway.

3. The system of claim 1, further comprising:
   a first supply line fluidly coupling the gas generator to a proximal end of the inlet passageway; and
   a second supply line fluidly coupling a distal end of the inlet passageway to the interior of the humidifier.

4. The system of claim 3, wherein the humidifier further comprises a mist chamber, and a distal end of the second supply line is disposed within the mist chamber.

5. The system of claim 3, further comprising a check valve coupled to the supply line.

6. The system of claim 1, further comprising a sensor for sensing sanitizing gas in the interior of the humidifier.

7. The system of claim 1, further comprising an exhaust system that is removably coupled to the connector unit, wherein the exhaust system comprises a filter.

8. The system of claim 1, further comprising a sealing system, wherein the sealing system provides a gas tight seal between a portion of a body of the connector unit and a surface of the opening.

9. The system of claim 8, wherein the sealing system is a flexible grommet.

* * * * *